(12) United States Patent
Shelton, IV et al.

(10) Patent No.: US 11,141,150 B2
(45) Date of Patent: Oct. 12, 2021

(54) BUTTRESS LOADER FOR SURGICAL STAPLERS

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US); Prudence Vulhop, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 746 days.

(21) Appl. No.: 15/436,221

(22) Filed: Feb. 17, 2017

(65) Prior Publication Data

US 2018/0235617 A1    Aug. 23, 2018

(51) Int. Cl.
| | |
|---|---|
| *A61B 17/072* | (2006.01) |
| *A61B 90/70* | (2016.01) |
| *A61B 50/20* | (2016.01) |
| *A61B 17/068* | (2006.01) |

(52) U.S. Cl.
CPC .......... *A61B 17/072* (2013.01); *A61B 17/068* (2013.01); *A61B 17/07292* (2013.01); *A61B 50/20* (2016.02); *A61B 90/70* (2016.02); *A61B 2017/07257* (2013.01); *A61B 2017/07271* (2013.01); *A61B 2017/07285* (2013.01)

(58) Field of Classification Search
CPC ....... A61B 90/70; A61B 17/072; A61B 50/20; A61B 17/068; A61B 17/07292; A61B 2017/07257; A61B 2017/07271; A61B 2017/07285; A61B 17/07257

USPC ....................................................... 227/176.1
See application file for complete search history.

(56) References Cited

U.S. PATENT DOCUMENTS

| | | | | |
|---|---|---|---|---|
| 3,595,187 A | * | 7/1971 | Gray ...................... | D05B 35/02 112/141 |
| 3,776,156 A | * | 12/1973 | Morgan ................. | D05B 35/02 112/141 |
| 5,752,965 A | * | 5/1998 | Francis ............ | A61B 17/07207 227/178.1 |

(Continued)

FOREIGN PATENT DOCUMENTS

| | | |
|---|---|---|
| EP | 2090252 A2 | 8/2009 |
| WO | WO-2013119365 A1 | 8/2013 |

OTHER PUBLICATIONS

International Search Report and Written Opinion for International App. No. PCT/US2018/017757 dated May 23, 2018 (9 pages).

*Primary Examiner* — Thanh K Truong
*Assistant Examiner* — Scott A Howell
(74) *Attorney, Agent, or Firm* — Mintz Levin Cohn Ferris Glovsky and Popeo, P.C.

(57) ABSTRACT

Various buttress loaders are provided for cleaning and affixing one or more buttresses to an end effector of a surgical stapler. In an exemplary embodiment, a buttress loader can be configured to clean at least one tissue-engaging surface of an end effector on a surgical stapler, and the buttress loader can be configured to attach a buttress to the at least one tissue-engaging surface of the end effector. For example, a buttress loader can have two slots configured to receive the end effector therein. One slot can be configured to clean the end effector, and the other slot can be configured to attach the buttress to the end effector.

19 Claims, 8 Drawing Sheets

(56) References Cited

U.S. PATENT DOCUMENTS

| | | |
|---|---|---|
| 6,939,358 B2 * | 9/2005 | Palacios .......... A61B 17/07207 |
| | | 606/151 |
| 7,143,925 B2 | 12/2006 | Shelton, IV et al. |
| 7,601,118 B2 | 10/2009 | Smith et al. |
| 8,317,070 B2 | 11/2012 | Hueil et al. |
| 8,393,514 B2 | 3/2013 | Shelton, IV et al. |
| 8,453,904 B2 * | 6/2013 | Eskaros .............. A61B 17/072 |
| | | 227/175.1 |
| 8,998,060 B2 * | 4/2015 | Bruewer .......... A61B 17/00491 |
| | | 227/176.1 |
| 9,282,962 B2 | 3/2016 | Schmid et al. |
| 2003/0120284 A1 | 6/2003 | Palacios et al. |
| 2005/0070929 A1 * | 3/2005 | Dalessandro .... A61B 17/07207 |
| | | 606/151 |
| 2013/0221065 A1 | 8/2013 | Aronhalt et al. |
| 2013/0256377 A1 | 10/2013 | Schmid et al. |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0134077 A1 | 5/2015 | Shelton, IV et al. |
| 2015/0272575 A1 | 10/2015 | Leimbach et al. |
| 2015/0277471 A1 | 10/2015 | Leimbach et al. |
| 2015/0351758 A1 | 12/2015 | Shelton, IV et al. |
| 2016/0089142 A1 | 3/2016 | Harris et al. |
| 2017/0055986 A1 | 3/2017 | Harris et al. |

* cited by examiner

BUTTRESS LOADER FOR SURGICAL STAPLERS

FIELD

Methods, devices, and systems are provided for cleaning and attaching a buttress to an end effector of a surgical device.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having a pair of movable opposed jaws formed on an end thereof for holding and forming staples therebetween. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut and/or open the stapled tissue between the stapled rows.

It can be beneficial to apply various medicants, buttresses, adjuncts, etc. to tissue at the surgical site. For example, leaks can occur due to the staple forming holes when penetrating the tissue or other object in which it is disposed, and various medicants, buttresses, and adjuncts can be used to prevent blood, air, gastrointestinal fluids, and other fluids from seeping through the openings formed by the staples. But it can be difficult to successfully clean the jaws and deliver these substances to the surgical site. Various medicants and/or buttresses can be added to one or both of the jaws of the surgical stapler, but that is difficult and time consuming to do. Thus there remains a need for improved devices and methods for applying buttresses to surgical staplers.

SUMMARY

Devices, methods, and systems are provided herein for cleaning and attaching a buttress to an end effectors of a surgical stapling device.

In one embodiment, a buttress loader is provided for use with a surgical stapler. The buttress loader can include a housing having a cleaning slot configured to seat a jaw of an end effector on a surgical stapler. The cleaning slot can have a cleaning material disposed therein and configured to clean a tissue-facing surface of the jaw. The housing can also include a loading slot configured to seat the jaw. The loading slot can have a buttress disposed therein, and the loading slot can be configured to release the buttress when the jaw is seated therein to thereby apply the buttress to the tissue-facing surface of the jaw.

In one embodiment, the jaw can be a first jaw and the end effector can include a second jaw. The cleaning slot can be configured to seat the first and second jaws with the cleaning material disposed therebetween, and the loading slot can be configured to seat the first and second jaws with the buttress disposed therebetween. The buttress can be a first buttress, and the loading slot can include a second buttress disposed therein.

In other aspects, the buttress loader can include a cover extending over at least one outward facing surface of the buttress. The cover can be configured to be automatically retracted into the housing when the jaw is inserted into the cleaning slot. In other embodiments, the cover can be manually removable.

The buttress loader can also include a retaining mechanism, such as retractable fingers, that are configured to release the buttress when the jaw is inserted into the loading slot.

In other aspects, the buttress can include an adhesive on an outward facing surface thereof such that the buttress is configured to adhere to the jaw when the jaw is seated in the loading slot. Alternatively or in addition, the buttress loader can include an adhesive applicator configured to apply adhesive to the buttress when the jaw is inserted into the cleaning slot.

In another embodiment, a buttress loading and stapling surgical system is provided and includes a surgical stapler having an elongate shaft with an end effector on a distal end thereof. The end effector can include a first jaw having a staple-containing cartridge, and a second jaw in the form of an anvil. The first and second jaws can be configured to clamp tissue therebetween. The system can also include a buttress loader having a cleaning material configured to be engaged between the first and second jaws to clean at least one of the first and second jaws, and at least one buttress configured to be engaged between the first and second jaws and to attach to a tissue-facing surface of at least one of the first and second jaws.

In one embodiment, the buttress loader can be configured to prevent release of the buttress until the cleaning material is engaged between the first and second jaws. For example, the buttress loader can include deflectable fingers configured to release the buttress as the buttress is engaged between the first and second jaws.

In other aspects, the buttress loader can be configured to apply an adhesive to the buttress in response to engagement of the cleaning material between the first and second jaws. Alternatively, the buttress can have an adhesive pre-disposed thereon such that the buttress configured to be attached to the surgical stapler by an adhesive.

In another embodiment, the buttress loader can include a protective cover disposed over at least a portion of the buttress. The protective cover can be configured to be manually removed, or it can be configured to automatically retract into the housing, e.g., in response to use of the cleaning slot.

Methods for cleaning a stapler and loading a buttress onto a stapler are provided. In one embodiment, the method can include engaging a cleaning material between first and second jaws of an end effector of a surgical stapler to thereby clean a tissue contacting surface of at least one of the first and second jaws. The method can further include engaging a buttress between the first and second jaws of the end effector such that the buttress attaches to the tissue contacting surface of at least one of the first and second jaws.

In one aspect, retaining features can release the buttress as the buttress is engaged between the first and second jaws.

In another aspect, after engaging the cleaning material between first and second jaws, the method can include retracting the first and second jaws in the engaged position relative to the cleaning material to thereby scrub the tissue contacting surface of at least one of the first and second jaws.

In another embodiment, a cover extending over the buttress can retract into the housing when the cleaning material is engaged between first and second jaws.

In other aspects, an adhesive on the buttress can adhere to the tissue contacting surface of at least one of the first and second jaws when the buttress is engaged between the first and second jaws. Alternatively, or in addition, an adhesive is applied to at least one surface of the buttress when the cleaning material is engaged between the first and second jaws.

BRIEF DESCRIPTION OF THE DRAWINGS

This invention will be more fully understood from the following detailed description taken in conjunction with the accompanying drawings, in which.

DETAILED DESCRIPTION

Figure 1:
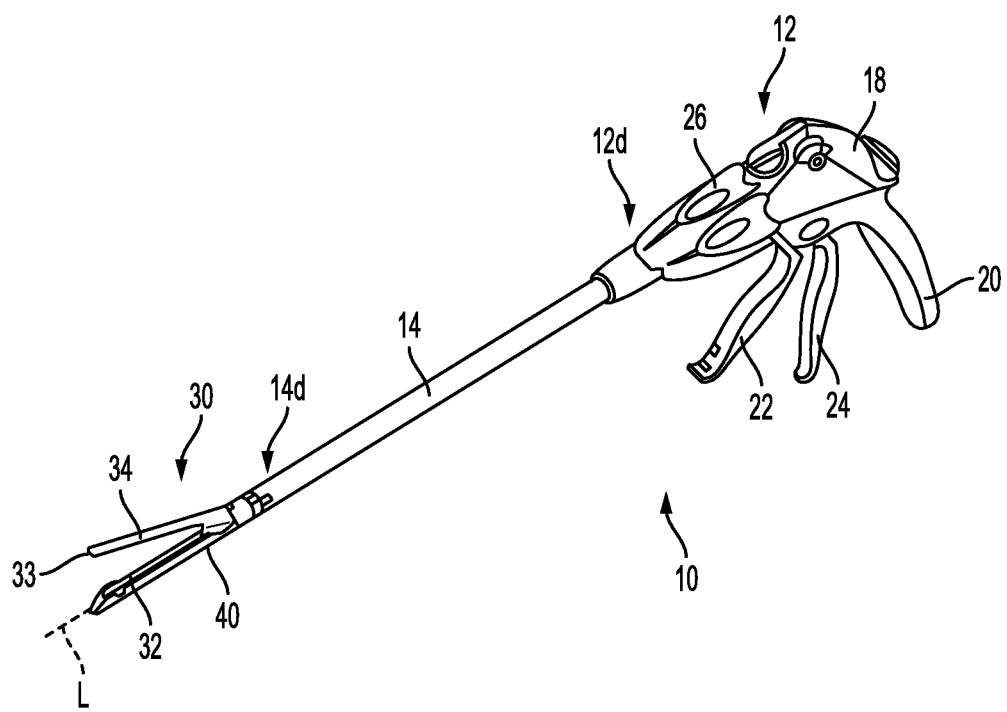
FIG. 1 is a perspective view of one embodiment of a surgical stapler.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Various buttress loaders are provided for cleaning and affixing a buttress to an end effector of a surgical stapling device. While the buttress loaders are described in connection with end effectors of surgical staplers, the buttress loaders can be used in connection with any type of surgical device. In an exemplary embodiment, a buttress loader can be configured to clean at least one tissue-engaging surface of an end effector on a surgical stapler, and the buttress loader can be configured to attach a buttress to the tissue-engaging surface of the end effector. For example, a buttress loader can have two slots, each configured to seat at least one jaw of the end effector therein. One slot can be configured to clean the end effector, and the other slot can be configured to attach the buttress to the end effector. The buttress loader can thus allow a user to rapidly clean and attach a buttress to a surgical stapler for use during an operation, increasing the speed and convenience of using buttresses with a surgical stapler.

As noted above, in certain aspects the buttress loaders disclosed herein can be used with a variety of surgical instruments, such as a surgical stapler. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The stapler can include a firing bar configured to drive the staples into tissue engaged between the jaws. The firing bar can include a knife or other cutting element capable of creating a cut between the staple rows along the tissue held within the jaws. The staplers can be used in a variety of different surgical procedures on a variety of tissues, for example in thoracic surgery or in gastric surgery.

Figure 2:
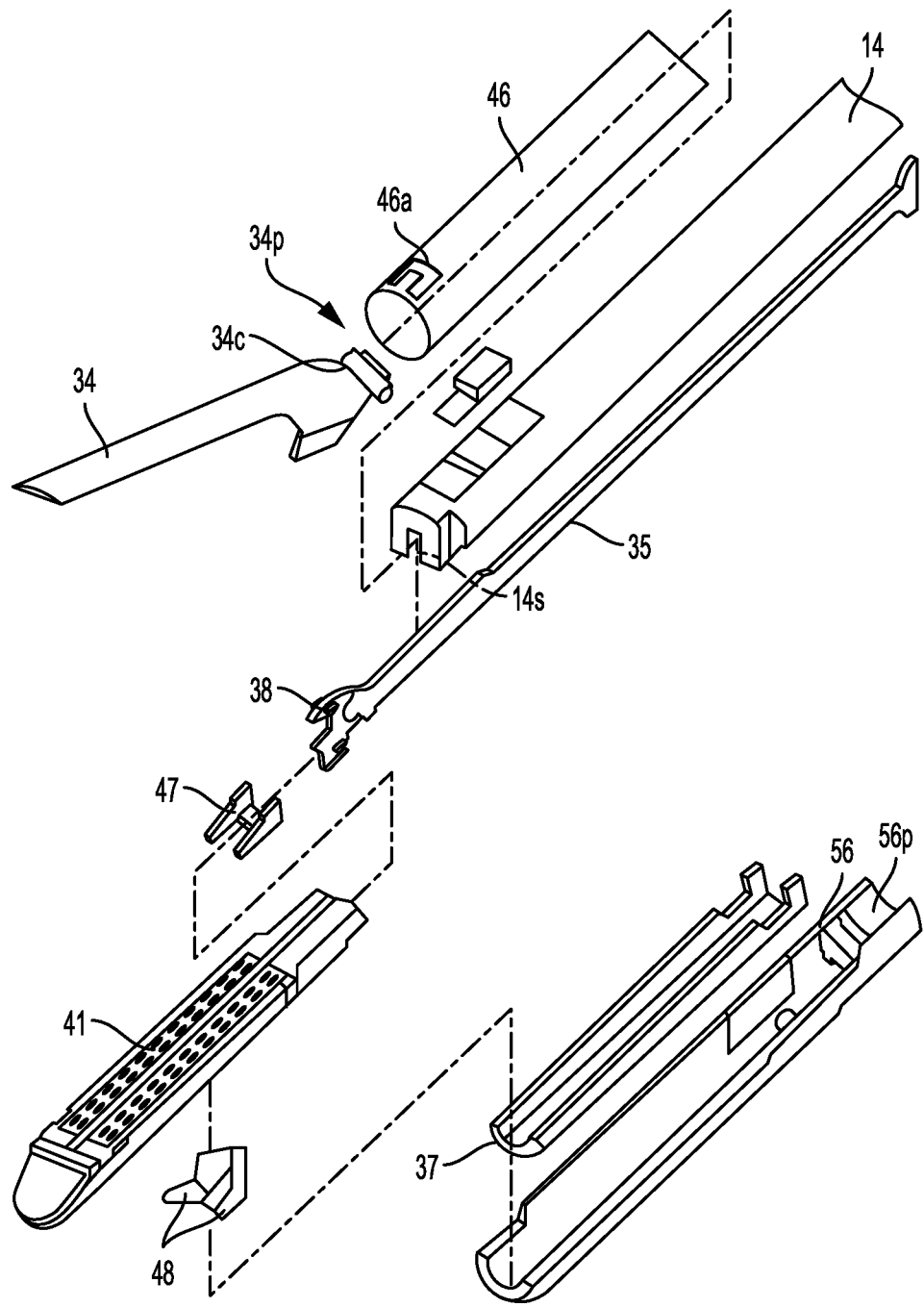
FIG. 2 is an exploded view of a distal portion of the surgical stapler of FIG. 1.

FIG. 1 illustrates one example of a linear surgical stapler 10 suitable for use with one or more of the buttress loaders disclosed herein. The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable. Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
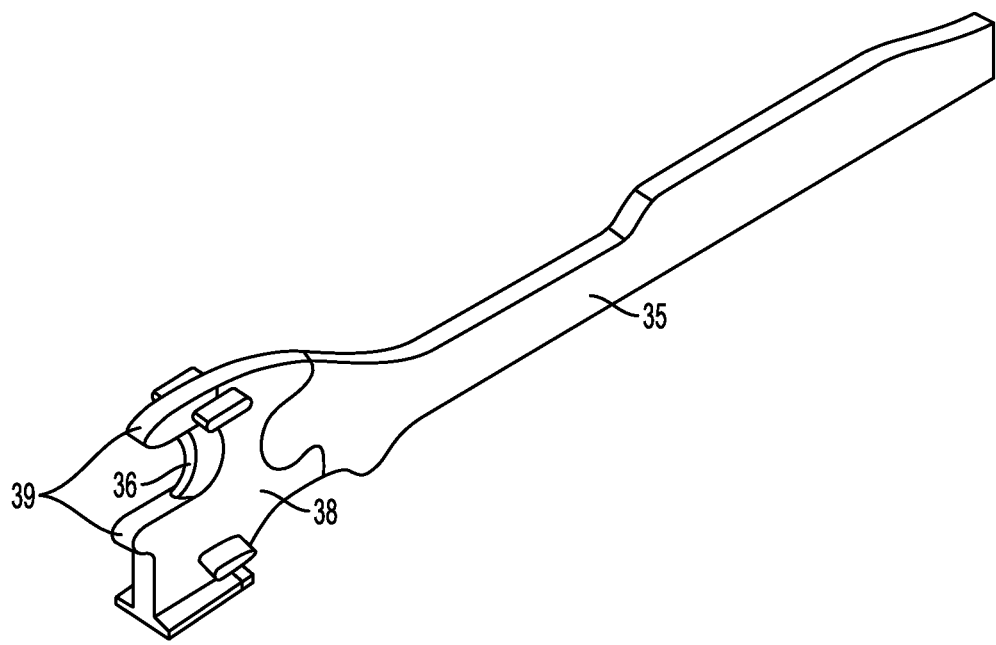
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
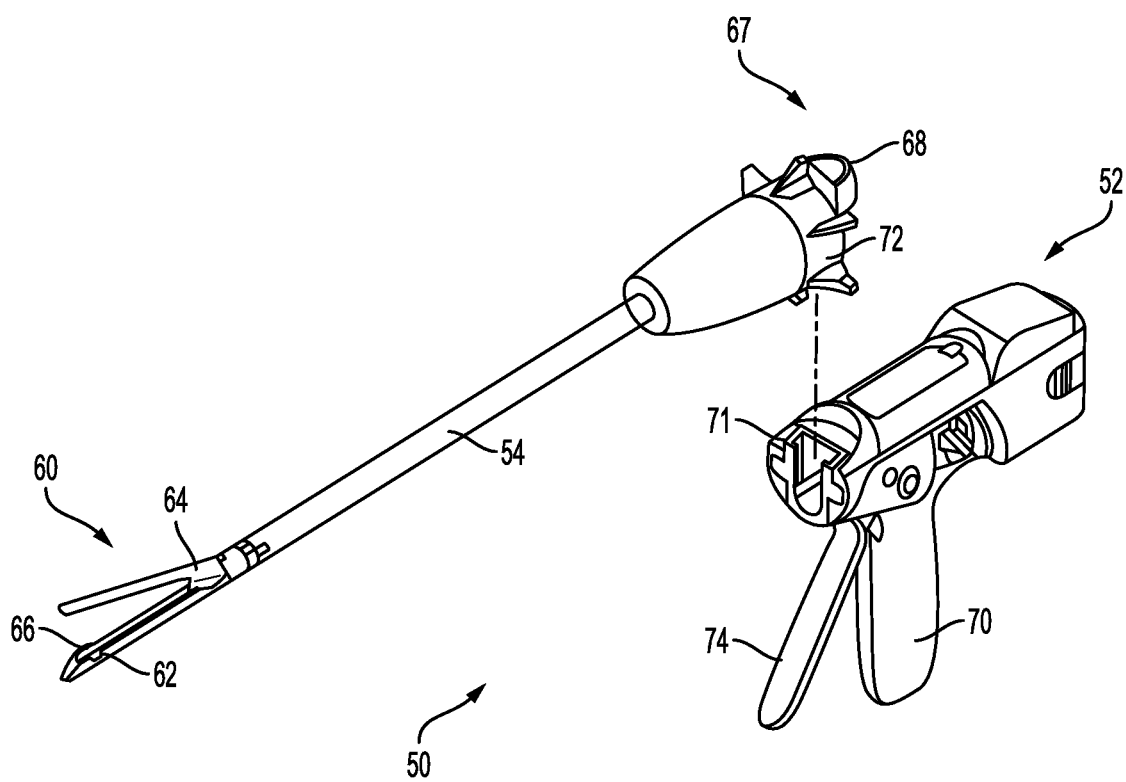
FIG. 4 is a perspective view of another embodiment of a surgical stapler.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

The illustrated examples of surgical stapling instruments 10, 50 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on November 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

A variety of different buttress(es), adjunct(s), and/or medicant(s) can be used with the variety of surgical instruments disclosed herein. "Adjuncts" are also referred to herein as "adjunct materials." It can be desirable to use one or more biologic materials and/or synthetic materials, collectively referred to herein as "adjuncts," in conjunction with surgical instruments to help improve surgical procedures. While a variety of different surgical end effectors can benefit from the use of adjuncts, in some exemplary embodiments the end effector can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s).

Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing). In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety. The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be adsorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue in-growth. The materials can include bioabsorbable and biocompatible polymers, including homopolymers and copolymers. Bioabsorbable polymers can be absorbable, resorbable, bioresorbable, or biodegradable polymers. An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Figure 5:
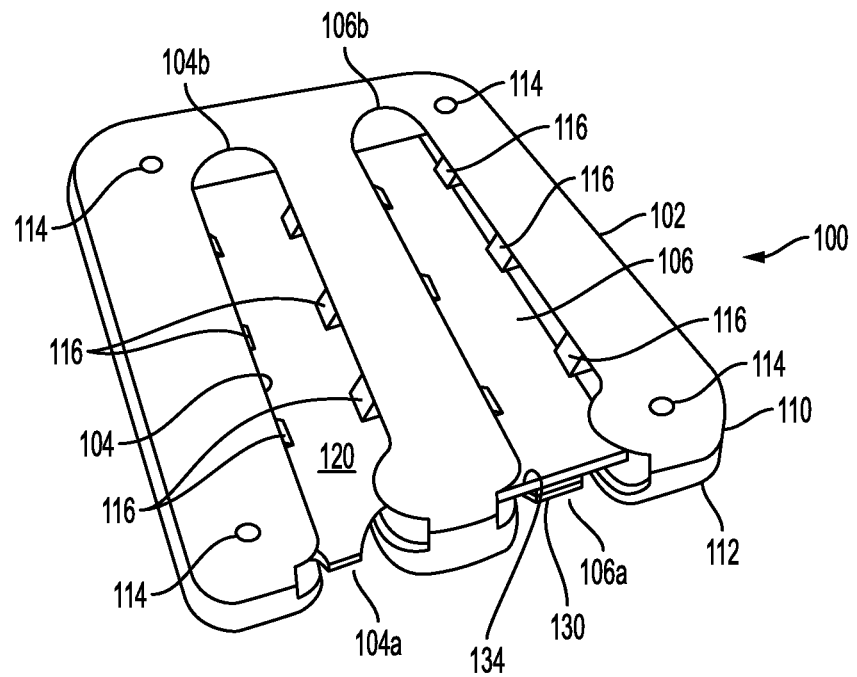
FIG. 5 is a perspective view of one embodiment of a buttress loader for use with a surgical stapler.
Figure 6:
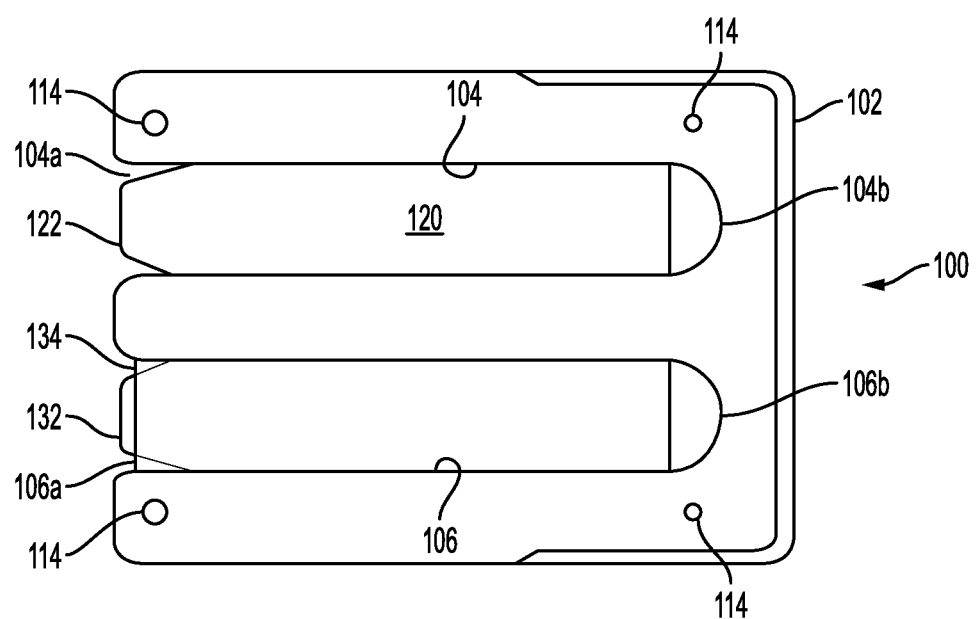
FIG. 6 is a top view of the buttress loader of FIG. 5.
Figure 7:
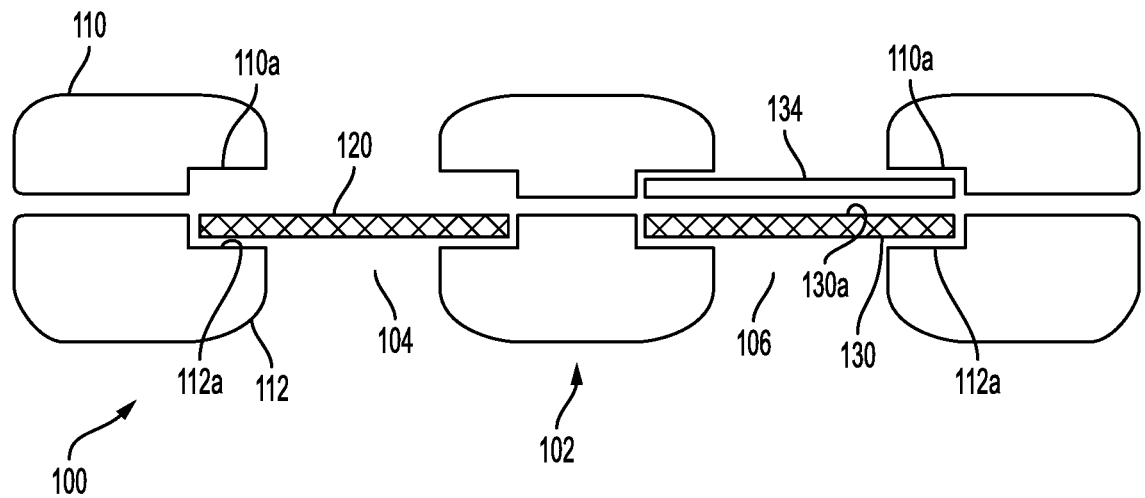
FIG. 7 is a cross-sectional side view of the buttress loader of FIG. 5.

Use of buttresses, adjuncts, and/or medicants with various surgical devices, such as surgical staplers, can necessitate cleaning the end effector and attaching a buttress, adjunct, and/or medicant to the surgical device for use in surgery. Cleaning the end effector and attaching the buttress can be achieved through a variety of techniques. FIGS. 5-7 illustrate one embodiment of a buttress loader 100. The illustrated buttress loader 100 has a frame 102, a cleaning slot 104, and a loading slot 106. The frame 102 can have any shape, such as a rectangular housing with a top portion 110 and a bottom portion 112. The top portion 110 and the bottom portion 112 can snap or clip together using, for example, posts 114 that extend from one of the top or bottom portions 110, 112 and snap into the other of the top or bottom portions 110, 112. In other embodiments, the two portions can be closed together in any number of ways, such as being glued, sealed, or formed as a single unit.

The frame 102 can have the cleaning slot 104 and the loading slot 106 formed therein. The cleaning slot 104 and the loading slot 106 can be configured to receive at least a portion of an end effector on a surgical stapler. For example, the slots 104, 106 can take the form of longitudinal openings formed in the frame 102 and can be sized and shaped to receive a linear end effector therein, such as the elongate jaws of the surgical staplers 10, 50. The slots 104, 106 can extend parallel to each other and can have open ends 104a, 106a on one side of the frame 102 and closed ends 104b, 106b on an opposite side of the frame 102. The closed ends 104b, 106b can have a semicircular shape, but a variety of different configurations are possible. The top portion 110 and the bottom portion 112 of the frame 102 can have ledges 110a, 112a formed along the slots 104, 106 and configured to create a groove that extends along a perimeter of at least the longitudinal edges of the slots 104, 106 when the top portion 110 and the bottom portion 112 are snapped together, as illustrated in FIG. 7.

Each slot 104, 106 can be configured to retain a material therein, such as a cleaning material or a buttress. In the illustrated embodiment, each of the top portion 110 and the bottom portion 112 of the frame 102 can have a plurality of fingers 116 that extend into the slots 104, 106. The fingers 116 can have a variety of shapes, such as a wedge shape with a triangular cross-section as illustrated in FIG. 5, and can be configured to retain material between the top portion 110 and the bottom portion 112 within the slots 104, 106. In the cleaning slot 104, the fingers 116 can be fixed and configured to remain in place even under a pulling or tugging force. In the loading slot 106, the fingers can be deflectable and/or spring biased to release material held therebetween under a pulling or tugging force. For example, the fingers 116 in the loading slot 106 can be configured to be retractable into the frame 102 when jaws of an end effector clamp onto a buttress therebetween. In some embodiments, the jaws can push the fingers 116 into the frame 102 when engaging the buttress thereby disengaging the fingers from the buttress and releasing the buttress from the loader 100.

The cleaning slot 104 can have a cleaning pad 120 that extends between the open end 104a and the closed end 104b of the cleaning slot 104. The cleaning pad 120 can have a variety of shapes, such as a rectangular shape. In an exemplary embodiment, the shape corresponds to the shape of an end effector to be cleaned, such as elongate jaws of a linear surgical stapler. The cleaning pad 120 can have a tongue 122 that extends from one end of the cleaning pad 120 and into the open end 104a of the cleaning slot 104. The cleaning pad 120 can extend the length between the two ends or can extend some distance less than entirely between the two ends, for example as illustrated in FIG. 6 in which the cleaning pad 120 terminates before reaching the closed end 104b. The cleaning pad 120 can extend into the groove formed by the ledges 110a, 112a and can be held between the top portion 110 and the bottom portion 112 of the frame 102 by the plurality of fingers 116. In some embodiments, the fingers can be configured to hold a buttress in the loading slot 106 (discussed in more detail below) while the cleaning pad 120 can be configured to be secured to the frame 102 through various other techniques. For example, the cleaning pad 120 can be configured to be secured with holes in the pad 120 that extend over pins in the frame 102. Other examples can include securing the cleaning pad 120 by the pad 120 being glued in place, welded in place, held in place by other posts from the housing 102 that are formed into mushrooms with heated tooling, etc.

The cleaning pad 120 can have a variety of configurations. For example, the cleaning pad 120 can be made from an abrasive material with a cleaning solvent saturated therein and configured to remove a variety of substances, such as adhesive, tissue, and/or oily residue. The cleaning pad 120 can be configured to remove any build-up and/or adhesive left on jaws (particularly an anvil) on an end effector left over from any previous firings with an adjunct. This cleaning can be beneficial to prevent any adhesive build up on the device, which can cause a variety of problems such as causing staples to be malformed, causing over-compression of tissue, etc. In various embodiments, a solution that aids in adhesion can also be added to the cleaning pad 120. The cleaning pad 120 can be configured to be engaged by opposed jaws on an end effector of a surgical stapler, and it can be configured to clean one side of the surgical stapler, such as the anvil side or to clean both sides as may be needed. In certain embodiments, the cleaning pad 120 can have various configurations, such as different sides of the pad with a cleaning side and a neutral side, different layers of the pad with a cleaning layer and a neutral layer, a cover or film on one side to prevent cleaning, etc.

The loading slot 106 can have a buttress 130, such as any of the buttresses, adjuncts, and/or medicants discussed above, Vicryl matrix, etc., disposed therein. The buttress 130 can have a variety of shapes, such as a rectangular shape. In an exemplary embodiment, the shape corresponds to the shape of an end effector to be cleaned, such as elongate jaws of a linear surgical stapler. The buttress 130 can have a tongue 132 that extends from one end of the buttress 130 and into the open end 106a of the loading slot 106. The buttress 130 can extend entirely between the open end 106a and the closed end 106b of the loading slot 106, or it can extend some distance less than entirely between the two ends, for example as illustrated in FIG. 6 in which the buttress 130 terminates before reaching the closed end 106b. The buttress 130 can be held between the top portion 110 and the bottom portion 112 of the frame 102 and can be held in place by the plurality of fingers 116 in the groove formed by the ledges 110a, 112a. The buttress 130 can be configured to be released by the fingers 116 upon application of a threshold force on the buttress 130 such that the buttress 130 will be free from the buttress loader 100. For example, the fingers 116 can defect out of the slot as the buttress 130 is engaged by jaws of an end effector to thereby release the buttress 130.

The buttress 130 can have a variety of configurations, as discussed above, and can have a variety of attachment mechanisms thereon, such as an adhesive coated on a surface of the buttress 130. A variety of adhesives can be used, such as 50-50 PCL-PGA, other absorbable polymers such as mixes of poloxamers, natural substances such as bees wax, etc. The adhesive can be spread on one or both surfaces of the buttress 130. For example, the buttress 130 can have an adhesive spread on upper surface 130a of the buttress 130 that is configured to contact a tissue-facing surface of a surgical stapler. A cover 134 can be disposed in the loading slot 106 with the buttress 130. The cover 134 can have a variety of configurations, such as a rectangular-shaped thin sheet of material that extends between the open end 106a and the closed end 106b of the loading slot 106 with the buttress 130. The cover 134 can be held between the top portion 110 and the bottom portion 112 of the frame 102 with the buttress 130 and can cover the adhesive surface 130a of the buttress 130. The cover can be made from a variety of materials. For example, the cover can be a compliant but non-porous material, various plastics, etc. The cover 134 can be configured to be manually removed, although a variety of different retraction options are possible. For example, the cover can be configured to automatically snap open upon use of the cleaning slot 106, be rolled up inside the buttress loader 100 by, for instance, having a pressure-sensitive rolling mechanism in the buttress loader 100 that is configured to sense clamping on the cleaning pad 120 and then trigger rolling or retraction of the cover from the buttress 130, etc.

In use, the jaws of a surgical stapler can first be clamped onto the cleaning pad 120 in the cleaning slot 104. With the end effector engaging the cleaning pad 120, the jaws of the surgical stapler can be pulled out of the slot 104. Because the surgical stapler is still clamped on the cleaning pad 120 as it is retracted, the cleaning pad 120 can scrub and clean the tissue facing surface of the anvil and/or the cartridge. In some embodiments, the cleaning pad 120 can be used to clean just the anvil side of a surgical stapler without cleaning the cartridge side, by using the various approaches discussed above. As the surgical stapler is retracted out of the slot 104, the fingers 116 or other retention mechanisms can retain the cleaning pad 120 in the cleaning slot 104. A user can remove the cover 134 from the loading slot 106 or it can be automatically removed upon cleaning, exposing the adhesive side 130a of the buttress. The user can clamp the surgical stapler onto the buttress 130 in the loading slot 106 with one of the anvil or the cartridge of the surgical stapler contacting the adhesive side 130a. The buttress 130 will attach to the tissue facing surface adjacent the adhesive, and the jaws can be retracted from the slot 106 after unclamping the jaws. Because the buttress 130 is attached to the surgical stapler, the buttress will be released from the buttress loader 130 upon application of a threshold force, for example by having the fingers 116 release the buttress 130 under application of force or by withdrawing the buttress 130 distally through the open end 106a of the loading slot 106. The buttress 130 is ready for delivery to tissue. Provided above is an embodiment of a single-step, two-stage buttress loader. Two step loaders are also possible, in which a user clamps a surgical stapler onto a first loader that only cleans the surgical stapler before clamping the surgical stapler onto a second, separate loader with a buttress that loads the buttress onto the surgical stapler (similar to the loading process described above).

Figure 8:
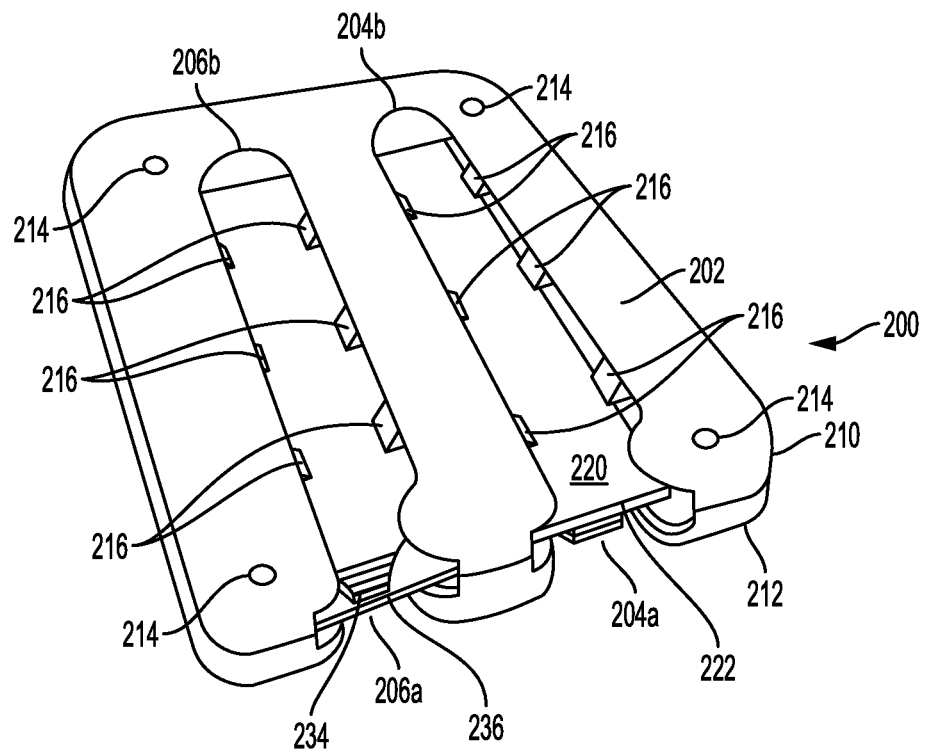
FIG. 8 is a perspective view of another embodiment of a buttress loader for use with a surgical stapler.
Figure 9:
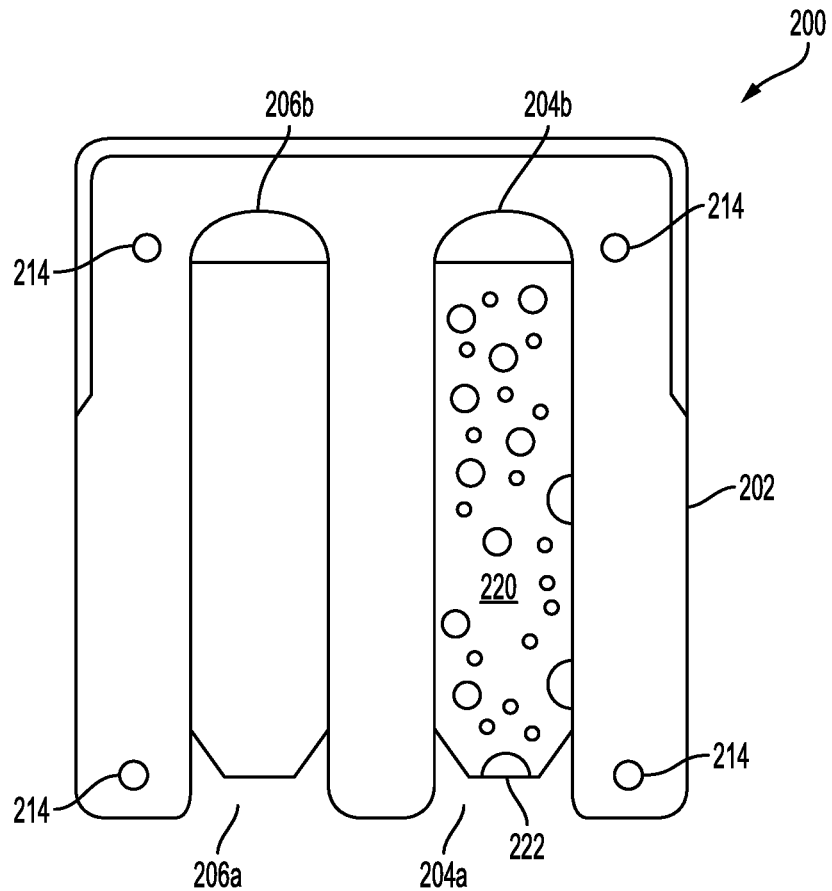
FIG. 9 is a top view of the buttress loader of FIG. 8.
Figure 10:
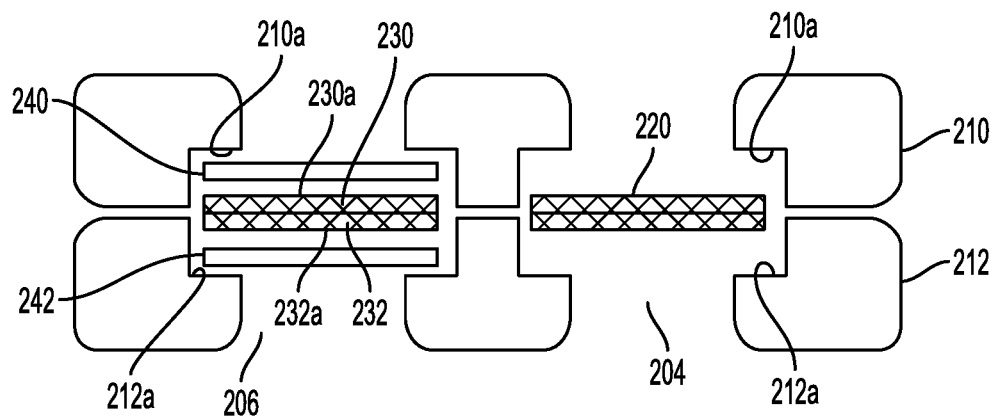
FIG. 10 is a cross-sectional side view of the buttress loader of FIG. 8.

The buttress loader 100 illustrates a buttress 130 designed to be attached to only one side of a surgical stapler, but a variety of other configurations are possible. For example, FIGS. 8-10 illustrate a buttress loader 200 that is similar to the buttress loader 100 discussed above. The buttress loader 200 can have a frame 202, a cleaning slot 204, and a loading slot 206. The frame 202 can have an approximate M shape with a top portion 210 and a bottom portion 212. The top portion 210 and the bottom portion 212 can snap or clip together using, for example, posts 214 that extend from one of the top or bottom portions 210, 212 and snap into the other of the top or bottom portions 210, 212. The frame 202 can have the cleaning slot 204 and the loading slot 206 formed therein. The slots 204, 206 can take the form of longitudinal openings formed in the frame 202 and can be sized and shaped to receive a linear end effector of a surgical stapler therein, such as the staplers 10, 50. The slots 204, 206 can extend parallel to each other and can have open ends 204a, 206a on one side of the frame 202 and closed ends 204b, 206b on an opposite side of the frame 202. The top portion 210 and the bottom portion 212 of the frame 202 can have ledges 210a, 212a formed along the slots 204, 206 and configured to create a groove that extends along at least the longitudinal edges of the slots 204, 206 when the top portion 210 and the bottom portion 212 are snapped together. Each of the top portion 210 and the bottom portion 212 of the frame 202 can have a plurality of fingers 216 that extend into the slots 204, 206. The fingers 216 can be configured to retain material between the top portion 210 and the bottom portion 212 within the slots 204, 206, as described above.

The cleaning slot 204 can have a cleaning pad 220, similar to cleaning pad 120, that extends between the open end 204a and the closed end 204b of the cleaning slot 204. The cleaning pad 220 can have a rectangular shape and a tongue 222 that extends from one end of the cleaning pad 220 and into the open end 204a of the cleaning slot 204. The cleaning pad 220 can be held between the top portion 210 and the bottom portion 212 of the frame 202 by the plurality of fingers 216 and/or other means described above and the groove formed by the ledges 210a, 212a. The cleaning pad 220 can be made from an abrasive material with a cleaning solvent saturated therein and configured to remove adhesive from previous firings, tissue, oily residue, etc. The cleaning pad 220 can be configured to have an end effector of a surgical stapler closed thereon and can be configured to clean both sides of the surgical stapler.

The loading slot 206 can have a first and second buttress 230, 232 similar to the buttress 130 discussed above. The first buttress 230 can be placed on top of the second buttress 232 in the loading slot 206. The buttresses 230, 232 can have rectangular shapes, and each buttress 230, 232 can have a tongue 234, 236 that extends from one end of the buttress 230, 232 adjacent the open end 206a of the loading slot 206. The buttresses 230, 232 can extend between the open end 206a and the closed end 206b of the loading slot 206. The buttresses 230, 232 can be held between the top portion 210 and the bottom portion 212 of the frame 202 by the plurality of fingers 216 and the groove formed by the ledges 210a, 212a. In other embodiments, the buttress can be configured to be secured to the loading slot in a variety of different ways. For example, these could include less adhesive or less-aggressive adhesive than on the device-contacting side of the adjunct, breakaway features that pull through holes in the adjunct, etc. The buttresses 230, 232 can be configured to be released by the fingers 216 upon application of a threshold force such that the buttresses 230, 232 will be free from the buttress loader 200. The buttresses 230, 232 can have a variety of configurations, as discussed above, and can have a variety of attachment mechanisms thereon, such as an adhesive. The adhesive can be spread on an outward-facing surface 230a, 232a of each of the buttresses 230, 232 so that each of the surfaces 230a, 232a are configured to attach to a tissue-facing surface of a surgical stapler. For example, the surface 230a of the first buttress 230 can be configured to adhere to an anvil of a surgical stapler, while the surface 232a of the second buttress 232 can be configured to adhere to a cartridge of the same surgical stapler. A first cover 240 can be disposed in the loading slot 206 in contact with the first buttress 230. The first cover 240 can be held between the top portion 210 and the bottom portion 212 of the frame 202 and can cover the adhesive surface 230a of the first buttress 230. A second cover 242 can be disposed in the loading slot 206 in contact with the second buttress 232. The second cover 242 can be held between the top portion 210 and the bottom portion 212 of the frame 202 and can cover the adhesive surface 232a of the second buttress 232. The covers 240, 242 can be made from a variety of materials, such as compliant but non-porous materials, various plastics, etc. The covers 240, 242 can be configured to be manually removed, although a variety of different retraction options are possible, as discussed above.

In use, an end effector of a surgical stapler can first be clamped onto the cleaning pad 220 in the cleaning slot 204. While the jaws are clamped, the surgical stapler can be pulled away from the buttress loader 200. The cleaning pad 220 can scrub and clean the tissue-facing surface of each jaw as it is removed. As the surgical stapler is pulled away from the buttress loader 200, the fingers 216 will retain the cleaning pad 220 in the cleaning slot 204. A user can remove the first and second covers 240, 242 from the loading slot 206, or they can retract automatically, exposing the adhesive sides 230a, 232a of the first and second buttresses 230, 232. The user can clamp the surgical stapler onto the buttresses 230, 232 such that the anvil of the surgical stapler closes on the adhesive side 230a of the first buttress 230, and the cartridge of the surgical stapler closes on the adhesive side 232a of the second buttress 230. Clamping can cause the fingers 216 to deflect, such as retracting into the frame 202. The first and second buttresses 230, 232 will attach to the jaws, and the surgical stapler can be unclamped and pulled away from the buttress loader 200. This motion will cause the buttresses 230, 232 to be pulled away as well, and the buttresses 230, 232 can then be deployed in an operation.

Figure 11:
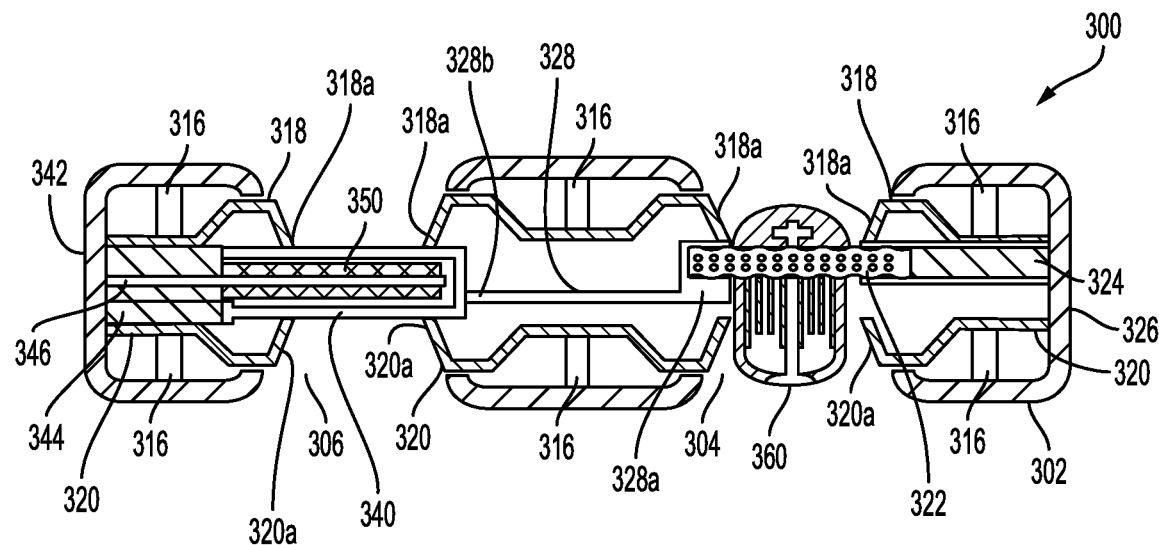
FIG. 11 is a cross-sectional side view of another embodiment of a buttress loader for use with a surgical stapler.
Figure 12:
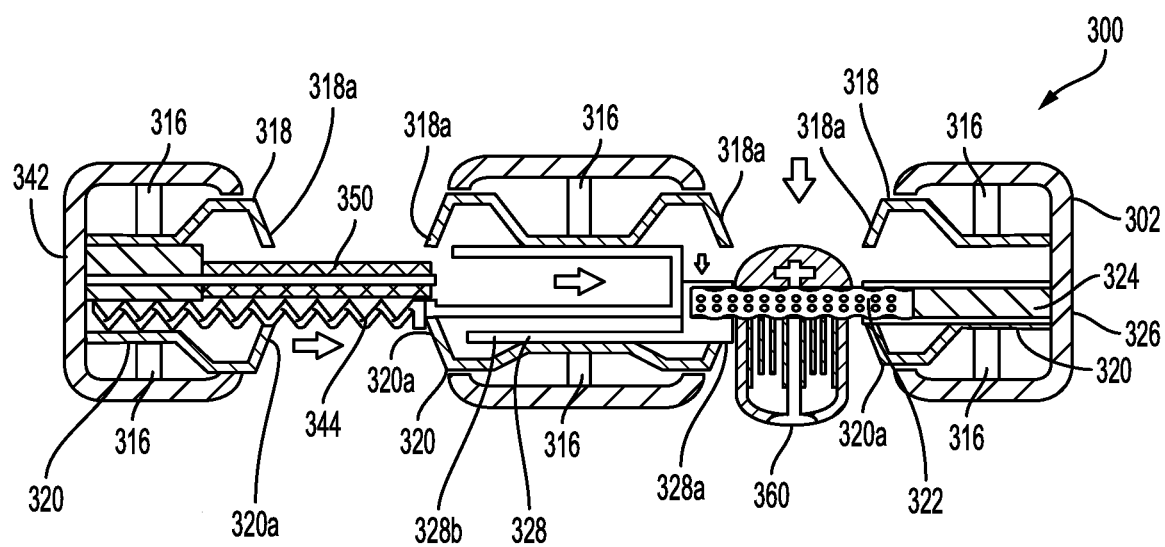
FIG. 12 is a cross-sectional side view of the buttress loader of FIG. 11.

While the covers can be manually removed, covers in other embodiments can be automatically retracted upon clamping of a surgical stapler on the cleaning pad. For example, FIGS. 11-12 illustrate a buttress loader 300 similar to the buttress loader 200. The buttress loader 300 can have a frame 302, a cleaning slot 304, and a loading slot 306. The frame 302 can have an approximate M shape and can have internal support structures. For example, posts 316 can extend inward from the frame 302 to provide support to an upper internal framework 318 and a lower internal framework 320. The upper and lower internal framework 318, 320 can extend throughout an interior of the frame 302 and be configured to provide support to material disposed within the slots 304, 306 and to facilitate receipt of the end effector. For example, the upper and lower internal framework 318, 320 can have angled ends 318a, 320a that extend at an angle into the slots 304, 306 to guide the jaws into the slots 304, 306. The slots 304, 306 can take the form of longitudinal openings formed in the frame 302 and can be sized and shaped to receive a linear end effector of a surgical stapler therein, such as the staplers 10, 50. The slots 304, 306 can extend parallel to each other and can have open ends on one side of the frame 302 and closed ends on an opposite side of the frame 302.

The cleaning slot 304 can have a cleaning pad 322, similar to cleaning pad 220, that extends between the open end 304a and the closed end 304b of the cleaning slot 304. A cleaning support structure 324 can be disposed in one of the outer legs of the M shaped frame 302, extending between an external wall 326 of the frame 302 and the cleaning pad 322, and it can be configured to hold a longitudinal edge of the cleaning pad 322 in the cleaning slot 304. On an opposite side of the cleaning pad 322 and disposed within the inner leg of the M shaped frame 302 is a movable lever 328 that has an approximately L shaped cross-sectional shape. A first end 328a holds a longitudinal edge of the cleaning pad 322 opposite to the cleaning support structure 324. The movable lever 328 extends through an interior of the frame 302 toward the loading slot 306. A second end 328b of the movable lever 328 can be disposed in contact with a buttress cover 330. The cleaning support structure 324 and the movable lever 328 are configured to move up and down together within the frame 302 and to be initially in contact with the angled ends 318a that extend at an angle into the cleaning slot 304.

The loading slot 306 can have a buttress 350 similar to the buttress 230 that extends between the open end 306a and the closed end 306b of the loading slot 306. A rectangular-shaped buttress support 346 can be disposed in one of the outer legs of the M shaped frame 302 on the opposite side to the cleaning support structure 324, extending from an external wall 342 of the frame 302 and into the loading slot 306, and it can be configured to hold the buttress 350 in the loading slot 306. A spring 344 can be disposed between the external wall 342 and the buttress cover 330 and inside the outer leg of the M shaped frame 302 with the buttress support 346.

The cleaning pad 322 can have a rectangular shape and a tongue that extends from one end of the cleaning pad 322 adjacent the open end 304a of the cleaning slot 304. The cleaning pad 322 can be held between the upper and lower internal framework 318, 320 and can be held in the cleaning slot 304 initially against the angled ends 318a. In one embodiment, the cleaning pad 322 can be made from an abrasive material with a cleaning solvent saturated therein and configured to remove tissue and oily residue. The cleaning pad 322 can be configured to have an end effector of a surgical stapler clamped thereon and it can be configured to clean one or both sides of the surgical stapler.

The buttress 350 can have first and second portions 350a, 350b similar to the buttresses 230, 232. The first portion 350a can be placed on top of the buttress support 346, and the second portion 350b can be placed on bottom of the buttress support 346. The first and second portions 350a, 350b can have rectangular shapes, and each portion 350a, 350b can have a tongue that extends adjacent the open end 306a of the loading slot 306. The first and second portions 350a, 350b of the buttress 350 can extend between the open end 306a and the closed end 306b of the loading slot 306. The buttress 350 can be held between the upper and lower internal framework 318, 320. The buttress 350 can have a variety of configurations, as discussed above, and can have a variety of attachment mechanisms thereon, such as an adhesive. The adhesive can be spread on an outward-facing surface of each of the first and second portions 350a, 350b so that each of the surfaces is configured to attach to a tissue-facing surface of a surgical stapler.

In this embodiment, the cross-sectional shape of the cover 340 is U shaped with upper and lower horizontal sidewalls and a shorter vertical sidewall extending therebetween. The cover 340 can be disposed in the loading slot 306 such that it surrounds the buttress 350. Each of the upper and lower sidewalls of the U shaped cover 340 can initially extend over the first and second portions 350a, 350b of the buttress 350 and can be configured to cover and protect the buttress 350 until use. The vertical sidewall of the U shaped cover 340 can be disposed within the interior of the inner leg of the M shaped frame 302 and can contact the second end 328b of the lever arm 328. Ends of the upper and lower sidewalls of the cover 340 opposite the vertical sidewall can extend into the outer leg of the M shaped frame 302 with the buttress support 346 and the spring 344, and one of the ends of the upper and lower sidewalls of the cover 340 can be disposed in contact with the spring 344.

Initially, the cleaning pad 322 can be held in an upper starting position in which the lever arm 328 and the cleaning support structure 324 support the cleaning pad 322 and both contact the angled ends 318a of the upper interior framework 318. The second end 328b of the lever arm 328 can extend through the interior of the frame 302 to the loading slot 306 and can contact the cover 340. The arm 328 can act on the cover 340 to force the cover toward the spring 344, keeping the spring 344 compressed between the cover 340 and the outer wall 342 and keeping the cover 340 over the buttress 350. When a surgical stapler, such as the stapler 360, clamps onto the cleaning pad 322, the movement causes the cleaning pad 322 to move downward. With movement of the cleaning pad 322, the cleaning support structure 324 and the lever arm 328 both move downward as well. As they move downward, the second end 328b of the lever arm 328 moves out of contact with the cover 340. As soon as the lever arm 328 is no longer in contact with the cover 340, the spring 344 decompresses and forces the cover 340 to move toward the cleaning slot 304 and out of the loading slot 306. The cover 340 will come to rest in the inner leg of the M shaped frame 302 with the lever arm 328, leaving the buttress 350 uncovered, as shown in FIG. 12. The spring 344 can be located at only a single point along the frame 302, so the spring 344 will not block access of a surgical stapler to either side of the buttress 350. In some embodiments, the spring can be anchor in a center position and can be held in a stretched state by the lever. When released, the spring can be configured to retract and pull the covers to the center position. In such embodiments, there is thus no concern with the spring being too off-center to pull the covers or be in the way of the buttresses. After a user finishes cleaning the end effector of the surgical stapler 360, the surgical stapler 360 can be clamped onto the buttress 350 so that the first and second portions 350a, 350b will each attach to opposite sides of the surgical stapler 360, as described above.

Figure 13:
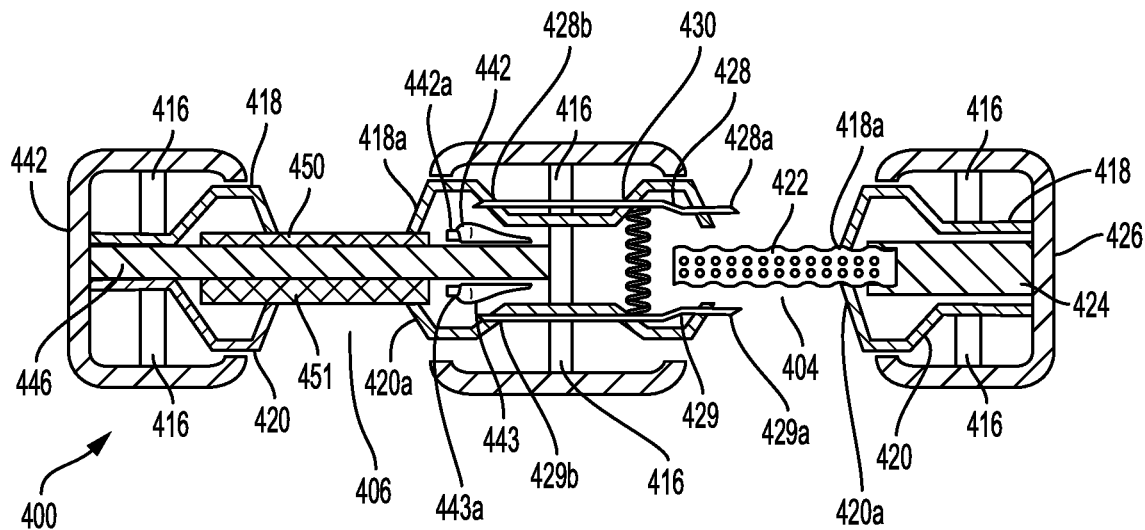
FIG. 13 is a cross-sectional side view of another embodiment of a buttress loader for use with a surgical stapler.
Figure 14:
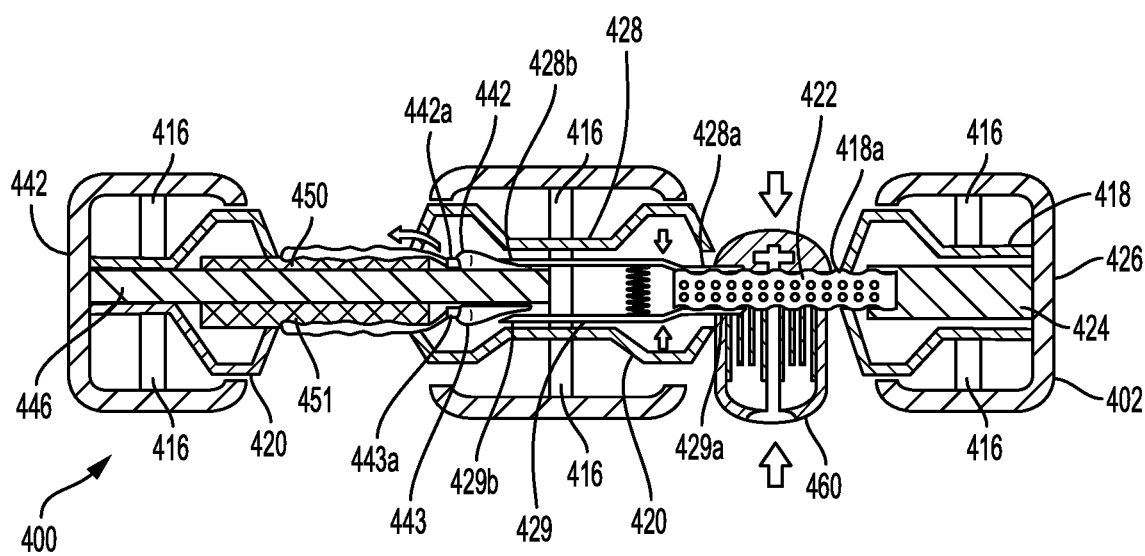
FIG. 14 is a cross-sectional view of the buttress loader of FIG. 13.

Some embodiments can lack covers while still protecting the buttress from being disturbed before a user is ready to attach the buttress to a stapler. For example, FIGS. 13-14 illustrate a buttress loader 400 similar to the buttress loader 300 but lacking a formal cover. The buttress loader 400 can have a frame 402, a cleaning slot 404, and a loading slot 406. The frame 402 can have an approximate M shape and can have internal support structures. For example, posts 416 can extend inward from the frame 402 to provide support to an upper internal framework 418 and a lower internal framework 420. The upper and lower internal framework 418, 420 can extend throughout an interior of the frame 402 and can be configured to provide support to material disposed within the slots 404, 406. For example, the upper and lower internal framework 418, 420 can have angled ends 418a, 420a that extend at an angle into the slots 404, 406 for engaging buttress or cleaning material, and for guiding jaws into the slots 404, 406. The cleaning slot 404 and the loading slot 406 can be formed in the frame 402. The slots 404, 406 can take the form of longitudinal openings through the frame 402 and can be sized and shaped to receive a linear end effector of the surgical stapler therein, such as the staplers 10, 50. The slots 404, 406 can extend parallel to each other and can have open ends on one side of the frame 402 and closed ends on an opposite side of the frame 402.

The cleaning slot 404 can have a cleaning pad 422, similar to cleaning pad 322, that extends between the open end 404a and the closed end 404b of the cleaning slot 404. A cleaning support structure 424 is disposed in one of the outer legs of the M shaped frame 402, extending between an external wall 426 of the frame 402 and the cleaning pad 422, and it can be configured to hold a longitudinal edge of the cleaning pad 422 in the cleaning slot 404. Unlike cleaning support structure 324, structure 424 is immovable and is fixed in place. On an opposite side of the cleaning pad 422 and disposed within the inner leg of the M shaped frame 402 are upper and lower levers 428, 429. The levers 428, 429 each have a long, rectangular shape and an arm 428a, 428b that extends into the cleaning slot 404. A spring 430 is disposed between the levers 428, 429 and biases the levers 428, 429 away from each other such that the upper lever 428 is configured to extend along the upper internal framework 418 and the lower lever 429 is configured to extend along the lower internal framework 420 in an initial position. The levers 428, 429 extend through an interior of the frame 402 toward the loading slot 406. Second ends 428b, 429b of the upper and lower levers 428, 429 are disposed above and below, respectively, upper and lower applicators 442, 443 with nozzles 442a, 443a that face into the loading slot 406. The upper and lower levers 429, 429 are configured to move up and down with application of force to the arms 428a, 429a that overcomes the spring force of spring 430.

The loading slot 406 can have upper and lower buttresses 450, 451, similar to buttress 350, that extends between the open end 406a and the closed end 406b of the loading slot 406. A rectangular-shaped buttress support 446 is disposed in one of the outer legs of the M shaped frame 402 on the opposite side to the cleaning support structure 424, extending from an external wall 442 of the frame 402 across the loading slot 406 and terminating in the inner leg of the M shaped frame 402, and it is configured to hold the buttresses 450, 451 in the loading slot 406.

The cleaning pad 422 can have a rectangular shape and a tongue that extends from one end of the cleaning pad 422 and adjacent the open end 404a of the cleaning slot 404. The cleaning pad 422 can be held between the upper and lower internal framework 418, 420 and between the arms 428a, 429a of the upper and lower levers 428, 429. In one embodiment, the cleaning pad 322 can be made from an abrasive material with a cleaning solvent saturated therein and configured to remove tissue and oily residue. The cleaning pad 422 can be configured to have an end effector of a surgical stapler closed thereon and can be configured to clean one or both sides of the surgical stapler, such as the anvil side.

The upper buttress 450 can be placed on top of the buttress support 446, and the lower buttress 451 can be placed on bottom of the buttress support 446. The buttresses 450, 451 can have rectangular shapes, and each one can have a tongue that extends adjacent the open end 406a of the loading slot 406. The buttresses 450, 451 can extend between the open end 406a and the closed end 406b of the loading slot 406. The buttresses 450, 451 can be held between the upper and lower internal framework 418, 420. The buttresses 450, 451 can have a variety of configurations, as discussed above, and can have a variety of attachment mechanisms. For example, the buttresses 450, 451 can have no attachment mechanism thereon, and instead can be positioned adjacent to the upper and lower applicators 442, 443.

Initially, as shown in FIG. 13, the upper and lower arms 428a, 429a are expanded above and below the cleaning pad 422. The second ends 428b, 429b can extend through the interior of the frame 402 to the loading slot 406 and are positioned above and below the upper and lower applicators 442, 443. The spring 430 keeps the upper and lower levers 429, 429 in this expanded configuration. When a surgical stapler, such as the stapler 460, clamps onto the cleaning pad 422, the stapler 460 clamps onto the arms 428a, 429a of the upper and lower levers 428, 429 and forces the arms 428a, 429a to move toward one another against resistance of the spring 430. The compressing movement of the arms 428a, 429a cause the upper and lower levers 428, 429 to move toward one another, causing the ends 428b, 429b to also move toward one another. The ends 428b, 429b compress against the upper and lower applicators 442, 443, causing adhesive to squirt from the nozzles 442a, 443a that face into the loading slot 406. An adhesive is thus applied to the outward facing surfaces of the buttresses 450, 451. A person skilled in the art will appreciate that multiple applicators can be disposed along the entire length of each buttress, as needed. After a user finishes cleaning the surgical stapler 460, the surgical stapler 460 can be clamped onto the upper and lower buttresses 450, 451 with the newly applied adhesive so that the upper and lower buttresses 450, 451 will each attach to opposite sides of the jaws of the surgical stapler 460.

While the adhesive is applied in this embodiment, other application methods are possible. For example, in some embodiments a heat activated or softened adhesive can be applied to the buttress. Clamping a surgical stapler onto a cleaning side of a buttress loader can activate a heater within the loader that can heat and/or apply a heat activated or softened adhesive to the buttress(es). For instance, the stapler can clamp onto the buttress, causing the loading slot to sense the presence of the stapler and hold the end effector while heating PDS attachment points that affix buttresses to one or both sides of the end effector. In such an embodiment, lights on the buttress loader (such as green and red LEDs) can indicate when the buttress(es) are attached and when the buttress loader releases the end effector.

The buttress loaders are not limited to horizontal configurations or manual cleaning and loading. For example, in some embodiments a box can be used with vertical slots. The first slot can have a cleaning system to clean the end effector, similar to the methods described above or incorporating a motor, solvents, scrub brushes, etc. Another slot could apply the buttress, similar to the methods described above or by a motorized process. In other embodiments activation of the cleaning step could automatically trigger the loading step. In various embodiments, cleaning and loading can be disposed in separate housings.

A person skilled in the art will appreciate that the present invention has application in conventional minimally-invasive and open surgical instrumentation as well application in robotic-assisted surgery.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A buttress loader for use with a surgical stapler, comprising:
   a housing having
      a cleaning slot configured to seat a jaw of an end effector on a surgical stapler, the cleaning slot having a cleaning material and a cleaning solution disposed therein and configured to clean a tissue-facing surface of the jaw, and
      a loading slot configured to seat the jaw, the loading slot having a buttress disposed therein, the buttress being formed from a different material than the cleaning material, the loading slot being configured to release the buttress when the jaw is seated therein to thereby apply the buttress to the tissue-facing surface of the jaw;
   wherein each of the cleaning and loading slots comprises an opening extending vertically entirely through the housing that is defined on three sides by the housing.

2. The buttress loader of claim 1, wherein the jaw comprises a first jaw and the end effector includes a second jaw, and wherein the cleaning slot is configured to seat the first and second jaws with the cleaning material disposed therebetween, and the loading slot is configured to seat the first and second jaws with the buttress disposed therebetween.

3. The buttress loader of claim 1, further comprising a cover removably matable to the housing and extending over at least one outward facing surface of the buttress in the loading slot,
   wherein the buttress includes an adhesive on the outward facing surface thereof such that the buttress is configured to adhere to the jaw when the jaw is seated in the loading slot.

4. The buttress loader of claim 3, wherein the cover is configured to be automatically moved out of the loading slot and into a cavity of the housing when the jaw is inserted into the cleaning slot.

5. The buttress loader of claim 1, wherein the cleaning and loading slots have angled fingers extending into each of the slots configured to secure the cleaning material and the buttress in the cleaning and loading slots.

6. The buttress loader of claim 1, further comprising a buttress support extending from an external wall of the housing and at least partially into the loading slot such that the buttress is at least partially supported thereby.

7. The buttress loader of claim 1, wherein each of the openings of the cleaning and loading slots is larger than the tissue-contacting surface of the jaw of the end effector.

8. The buttress loader of claim 3, wherein the cover has upper and lower horizontal sidewalls and a shorter vertical sidewall extending therebetween such that the cover has a U shaped cross section, the cover being configured to receive the buttress between the upper and lower horizontal sidewalls.

9. The buttress loader of claim 4, wherein the cavity of the housing configured to receive the cover is positioned between the cleaning and loading slots.

10. The buttress loader of claim 4, wherein the cover is spring-biased to be movable into the cavity of the housing.

11. The buttress loader of claim 4, further comprising a lever movably extending within an interior of the housing between the cleaning and loading slots, a first end of the lever being disposed in contact with the cleaning material in the cleaning slot, a second end of the lever being disposed in contact with the cover, the lever being configured to assist in moving the cover into the cavity of the housing when the jaw is inserted into the cleaning slot.

12. A buttress loader for use with a surgical stapler, comprising:
a housing with a top surface and a bottom surface having
a cleaning slot configured to seat a jaw of an end effector on a surgical stapler, the cleaning slot having a cleaning material and a cleaning soluiton disposed therein and configured to clean a tissue-facing surface of the jaw, and
a loading slot configured to seat the jaw, the loading slot having a buttress disposed therein, the buttress being formed from a different material than the cleaning material, the loading slot being configured to release the buttress when the jaw is seated therein to thereby apply the buttress to the tissue-facing surface of the jaw,
wherein the cleaning and loading slots are longitudinal openings that extend entirely through the housing from the top surface to the bottom surface and that are defined by the housing.

13. The buttress loader of claim 12, wherein each of the cleaning and loading slots has a first open end on one side of the housing and a second closed end on an opposite side of the housing.

14. The buttress loader of claim 12, wherein the jaw comprises a first jaw and the end effector includes a second jaw, and wherein the cleaning slot is configured to seat the first and second jaws with the cleaning material disposed therebetween, and the loading slot is configured to seat the first and second jaws with the buttress disposed therebetween.

15. The buttress loader of claim 12, wherein the housing has angled fingers extending into each of the cleaning and loading slots configured to secure the cleaning material and the buttress in the cleaning and loading slots.

16. The buttress loader of claim 12, further comprising a buttress support extending from an external wall of the housing and at least partially into the loading slot such that the buttress is at least partially supported thereby.

17. The buttress loader of claim 12, further comprising a cover extending over at least one outward facing surface of the buttress, the outward facing surface of the buttress having an adhesive thereon such that the buttress is configured to adhere to the jaw when the jaw is seated in the loading slot.

18. The buttress loader of claim 17, wherein the cover is configured to be automatically moved out of the loading slot and into a cavity of the housing when the jaw is inserted into the cleaning slot.

19. The buttress loader of claim 17, wherein the cover is movable between a first covering configuration in which the cover extends over the at least one outward facing surface of the buttress and a second retracted configuration in which the cover is received entirely within a cavity of the housing to expose the at least one outward facing surface of the buttress to the tissue-facing surface of the jaw.

* * * * *